United States Patent
Johnson (10) Patent No.: US 6,641,550 B1
(45) Date of Patent: Nov. 4, 2003

(54) ORTHOPEDIC SUPPORT FOR THE TREATMENT OF HEEL PAIN

(76) Inventor: Kerry Johnson, 13037 Charleston Way, Rosemount, MN (US) 55068

(*) Notice: Subject to any disclaimer, the term of this patent is extended or adjusted under 35 U.S.C. 154(b) by 0 days.

(21) Appl. No.: 10/160,824

(22) Filed: May 31, 2002

(51) Int. Cl.⁷ ................................................ A61F 13/00
(52) U.S. Cl. ...................................................... 602/65
(58) Field of Search ............................. 602/27–29, 65, 602/61, 60, 23, 5; 128/882

(56) References Cited

U.S. PATENT DOCUMENTS

| | | | | |
|---|---|---|---|---|
| 4,166,460 A | * | 9/1979 | Applegate | 602/27 |
| 4,844,058 A | * | 7/1989 | Vogelbach | 602/27 |
| 4,869,267 A | * | 9/1989 | Grim et al. | 602/27 |
| 4,878,504 A | * | 11/1989 | Nelson | 602/27 |
| 4,962,768 A | * | 10/1990 | Stromgren et al. | 602/27 |
| 5,372,576 A | * | 12/1994 | Hicks | 602/27 |
| 5,393,303 A | * | 2/1995 | Shiono | 602/27 |
| 5,472,411 A | * | 12/1995 | Montag et al. | 602/23 |
| 5,472,414 A | * | 12/1995 | Detty | 602/27 |
| 5,676,641 A | * | 10/1997 | Arensdorf et al. | 602/27 |
| 5,799,659 A | | 9/1998 | Stano | 128/882 |
| 5,822,887 A | * | 10/1998 | Turner | 36/89 |
| 5,865,779 A | | 2/1999 | Gleason | 603/30 |
| 6,117,098 A | * | 9/2000 | Weber et al. | 602/27 |
| 6,142,967 A | | 11/2000 | Couch | 602/66 |

* cited by examiner

Primary Examiner—Nicholas D. Lucchesi
Assistant Examiner—Huong Q. Pham
(74) Attorney, Agent, or Firm—Vidas, Arrett & Steinkraus, P.A.

(57) ABSTRACT

A method and device for treating heel pain comprises a first support mechanism for disposition about the heel region of a human foot and a secondary support mechanism for disposition about an arch region of a human foot. When disposed about the heel region and arch region respectively, the first support mechanism and the second support mechanism support the plantar fascia in a more normal biomechanical position.

10 Claims, 8 Drawing Sheets

ORTHOPEDIC SUPPORT FOR THE TREATMENT OF HEEL PAIN

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

Heel pain is a commonly reported foot complaint. Millions of cases are reported in the U.S. each year. Of the reported cases, roughly half are from individuals who have had heel pain for over a year.

Many of the reported complaints of heel pain are caused by or are related to the medical condition known as plantar fasciitis.

Plantar fasciitis and heel spurs are sometimes used as synonyms by the medical profession. However they are not the same. Plantar fasciitis can be a precursor to the development of a spur. Heel spurs develop as a result of chronic stress, wherein the body lays down calcium in response to irritation. Heel spurs are often sub-clinical. As many as 30% of the population have heel spurs and don't know it. It is usually plantar fasciitis that brings people to the doctor. The plantar fascia is a type of connective tissue that acts like a bowstring in connecting the forefoot (metatarsals) to the calcaneal bone of the heel. It aids other musculature on the underside of the foot to uphold the arch.

2. Description of the Related Art

Orthotics, orthopedic supports, taping procedures, and other devices and methods of treatment have been developed for the treatment of heel pain resulting from heel spurs/plantar fasciitis. For example:

In U.S. Pat. No. 6,142,967 a heel pain relief method and brace are described wherein it is proposed that heel pain may be addressed by a support designed to draw the heel medialward by pulling a strap around the bottom of the heel from lateral to medial and fastening it to the sleeve of the brace.

In U.S. Pat. No. 5,865,779 an elastic sock is described which is designed to support the foot longitudinally utilizing elastic material, thereby reducing stress to the plantar fascia. The effectiveness of the sock is based on the premise that heel pain is caused by a stretching of the plantar fascia longitudinally.

U.S. Pat. No. 5,799,659 describes addressing heel pain caused by a contracture of the calf muscle. This support is designed to create an acute angle between the foot and the lower leg while the patient is sleeping. This presumably assists in lengthening the calf muscle, thereby reducing stress on the plantar fascia.

The entire content of all of the patents listed within the present patent application are incorporated herein by reference.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to several embodiments for addressing and relieving heel pain in an individual, particularly heel pain caused by plantar fasciitis.

In at least one embodiment, the invention is directed to a method for treating plantar fasciitis wherein a support member or primary support mechanism, such as athletic tape, is wrapped around the calcaneal bone of the heel in a very tight manner to support the area of the plantar fascia where it inserts into the calcaneal bone of the heel.

In at least some embodiments a secondary support mechanism is utilized to support the plantar fascia medially.

In some embodiments, the invention is directed to a unique brace or sock, which incorporates both of a primary support mechanism and a secondary support mechanism in a single wearable unit. Preferably, the sock may be worn beneath other footwear such as a shoe or boot.

Further aspects of the invention will become apparent form the detailed description which follows.

BRIEF DESCRIPTION OF THE SEVERAL VIEWS OF THE DRAWINGS

A detailed description of the invention is hereafter described with specific reference being made to the following drawings.

DETAILED DESCRIPTION OF THE INVENTION

Figure 1:
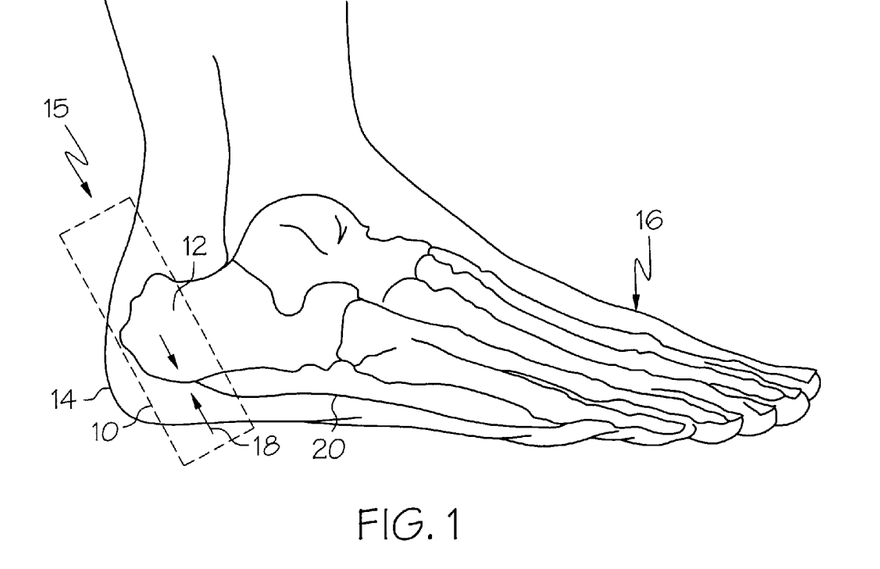
FIG. 1 is a side view of an embodiment of the invention as applied to a human foot.

As stated above the present invention may be embodied in many forms. For example, in FIG. 1 a first embodiment of the invention is depicted wherein athletic tape or other type of securement strap, member or members 10 comprise a primary support mechanism 15 for supporting the plantar fascia 20 where it engages the calcaneus 12 of the heel 14 of a human foot 16. In at least one embodiment, the member 10 is a material having little elasticity that is wrapped tightly around the heel 14 to apply a primary compressive force of support, indicated by arrows 18 to the heel 14. This compressive force acts to support the plantar fascia 20 thereby aiding in the direct alleviation of heel pain brought on by plantar fasciitis.

Figure 2:
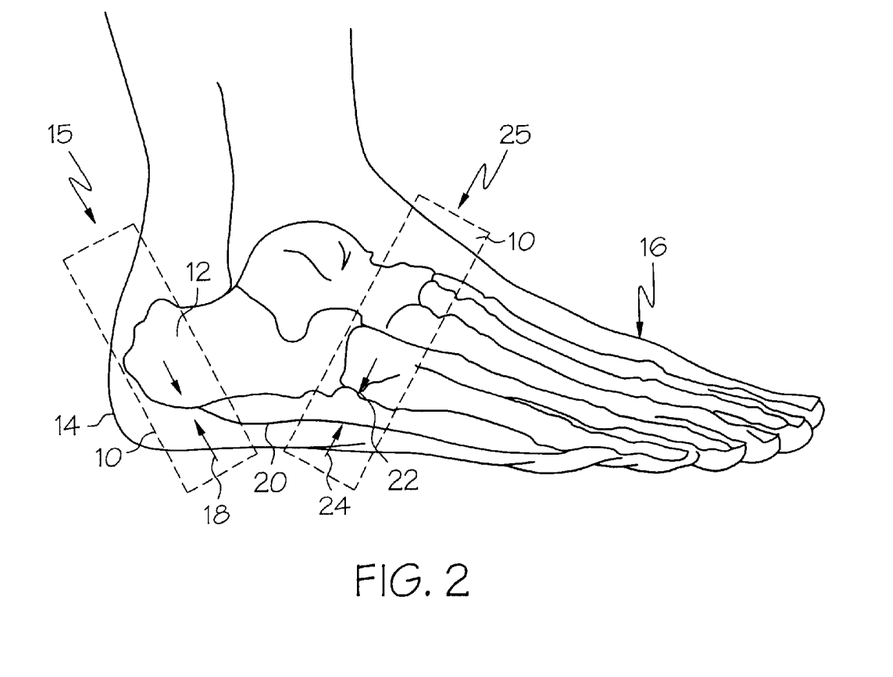
FIG. 2 is a side view of an embodiment of the invention as applied to a human foot.

In another embodiment of the invention, shown in FIG. 2, a secondary support mechanism 25 is utilized with the primary support mechanism 15. In the present embodiment, the secondary support mechanism 25 is disposed about the arch 22 of the foot 16 in order to provide a secondary compressive force of support such as is indicated by arrows 24.

The secondary support mechanism 25 may also be comprised of a member or members 10 as previously discussed above. However, in at least one embodiment, the secondary support mechanism 25 is constructed of a member or members 10 that is at least somewhat elastic to allow for foot splaying during the push-off phase of gait. The secondary support mechanism 25 is pulled up and around the medial aspect of the foot whereupon the secondary support mechanism 25 is attached to the ankle region 44.

The combination of the primary support mechanism 15 and the secondary support mechanism 25, provides the foot 16, and particularly the plantar fascia 20 and the surrounding musculature, with in a more normal biomechanical position, thereby facilitating healing of the plantar fascia and/or heel spur.

While taping or wrapping the foot with members 10 may provide a patient with desired pain relief and treatment of plantar fasciitis, proper taping or wrapping with members 10 may be compromised particularly due to the shape of the foot, and individual patient's intolerances and/or comfort levels.

Figure 3:
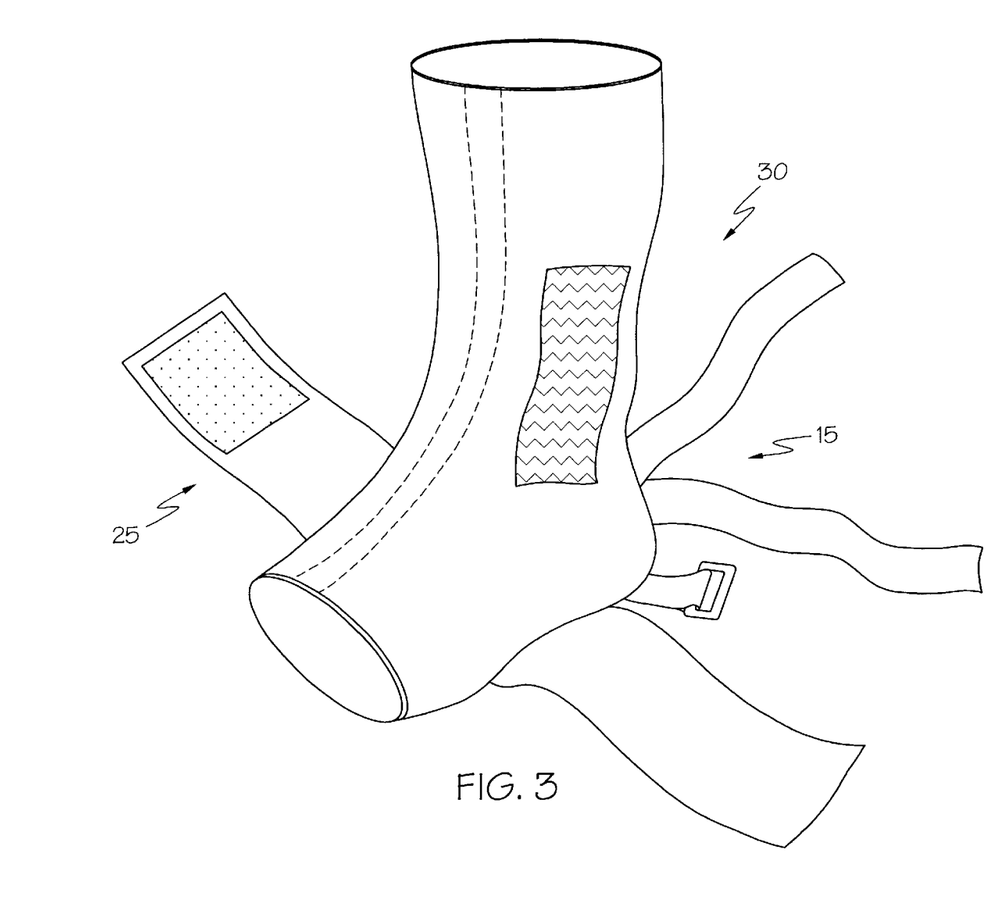
FIG. 3 is a perspective view of an embodiment of the invention directed to a unique sock or boot for addressing plantar fasciitis wherein the sock is shown in the unsecured state.
Figure 4:
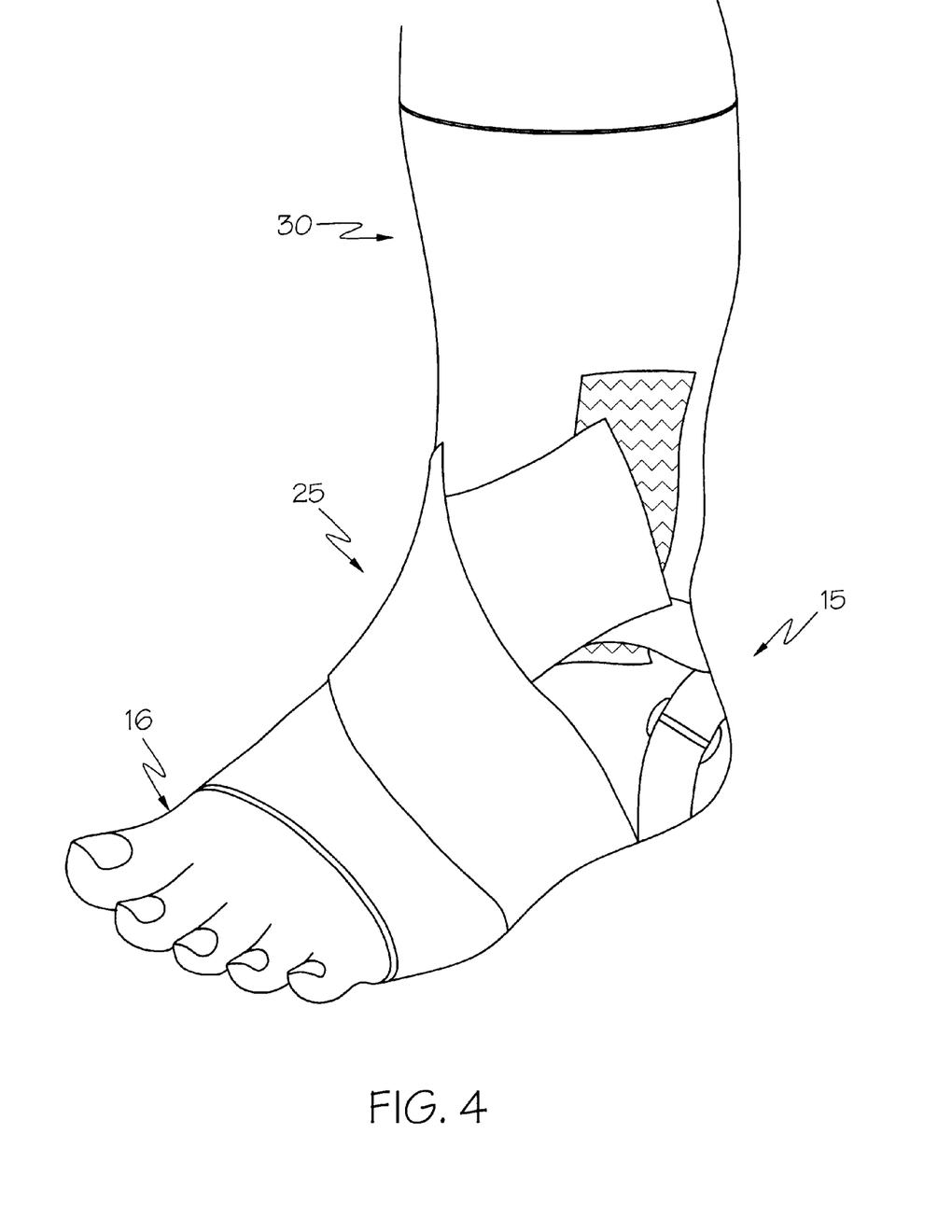
FIG. 4 is a perspective view of the embodiment shown in FIG. 3 wherein the sock is shown in the secured state about a human foot.

In order to provide a patient with the plantar fasciitis treatment described above without the need to repeatedly tape the foot with athletic tape of other individual securement members, an embodiment of the invention is shown in FIGS. 3 and 4, which provides an adjustable sock or boot 30 that may be comfortably worn on the patient's foot while providing both a primary support mechanism 15 and a secondary support mechanism 25. In FIG. 3, the sock 30 is shown prior to being placed over a foot wherein the support mechanisms are shown in the unengaged or unsecured position. In FIG. 4, the sock 30 is shown placed on a foot 16 wherein both the primary support mechanism 15 and the secondary support mechanism 25 are shown in a secured or engaged position thereabout.

In the embodiment shown in FIGS. 3 and 4 the support mechanisms 15 and 25 may comprise a variety of straps or bands that may be secured to the body of the sock in a variety of manners. As a result, the support mechanisms 15 and 25 may be adjusted for a variety of anatomical differences and comfort levels.

Figure 5:
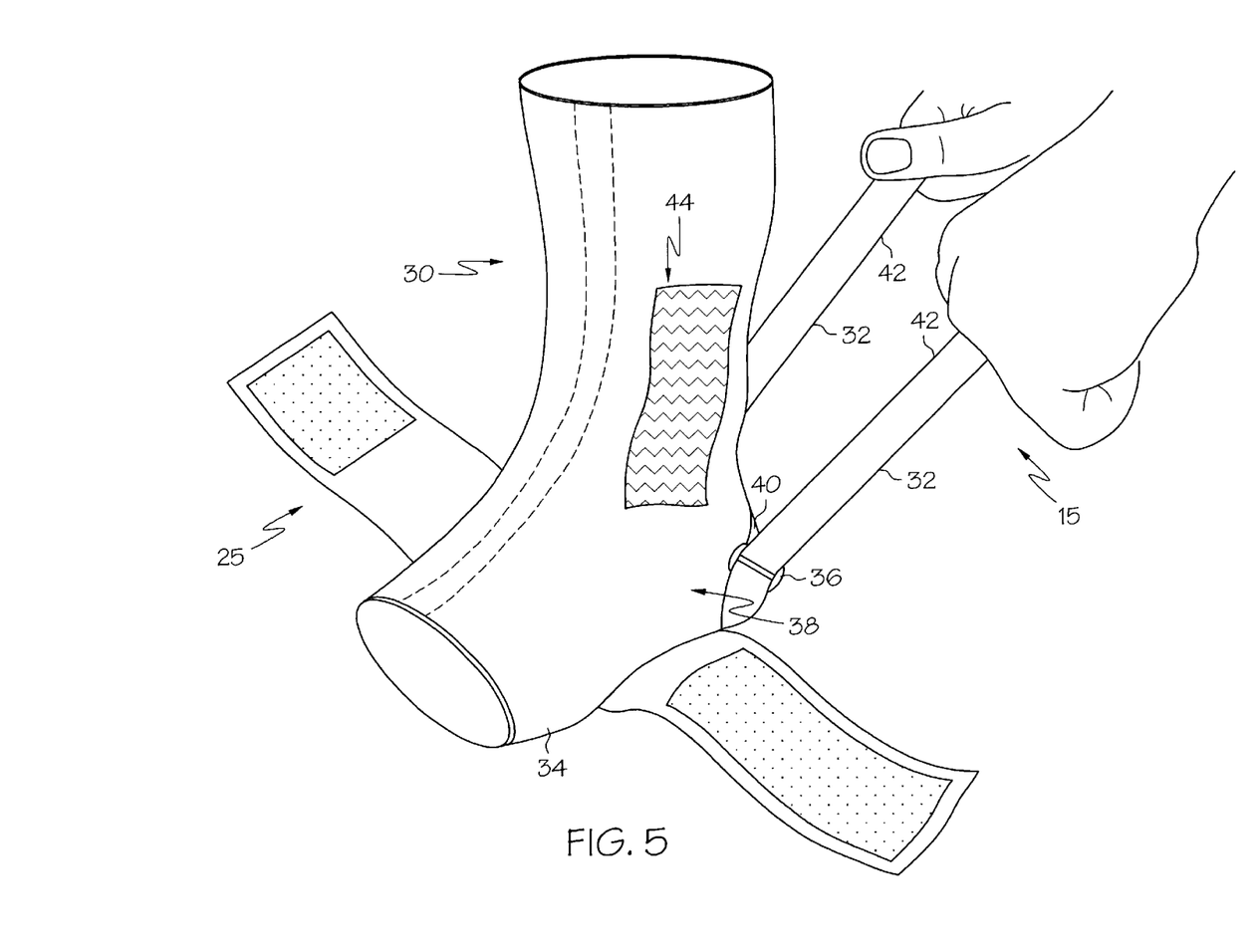
FIG. 5 is a perspective view of the embodiment shown in FIG. 3 wherein the sock is shown with the primary support mechanism being initially secured.

For example, in an embodiment of the invention shown in FIG. 5 the primary support mechanism 15 comprises one or more securement straps 32 each having an end fixedly engaged to the body 34 of the sock 30. In the embodiment shown, the primary support mechanism 15 further comprises an adjustment clasp, fastener or bracket 36 through which the strap or straps 32 are threaded to provide the heel region 38 of the sock 30 with an adjustable loop 40 thereabout. The loop 40 may be loosened or tightened as desired by adjusting the length of the straps 32 relative to the bracket 36 and then puling the free ends 42 of the straps 32 tight.

In the embodiment shown the straps are constructed of any material having sufficient material strength to be tightly wound through the bracket 36 and about a heel of an individual. Preferably the straps 32 are constructed of nylon, cotton, or other materials such as: canvas, and/or vinyl, etc. In some embodiments it may also be desirable to provide straps 32 or at least a portion thereof with a more flexible or elastic material such as: laminate material, neoprene, latex, Tietex®, Ultrilure®, elastic cotton, rubber, foam rubber, etc. Materials such as these may be sewn or woven into straps 32 as well as flaps 50 which are provided for in detail below. The straps 32 must be sufficiently inflexible so as to provide a fairly tight tension or compressive force of support about the heel.

The body 34 of the sock 30 may be constructed of a relatively flexible material such as latex-vinyl material such as neoprene. Preferably a single size sock will have sufficient elasticity to be capable of stretching to accommodate a range of foot sizes. However socks may be constructed in different sizes and shapes as may be desired or necessary. Other materials suitable for use in construction of the body 34 include but are not limited to those provided above for the construction of straps 32.

Figure 6:
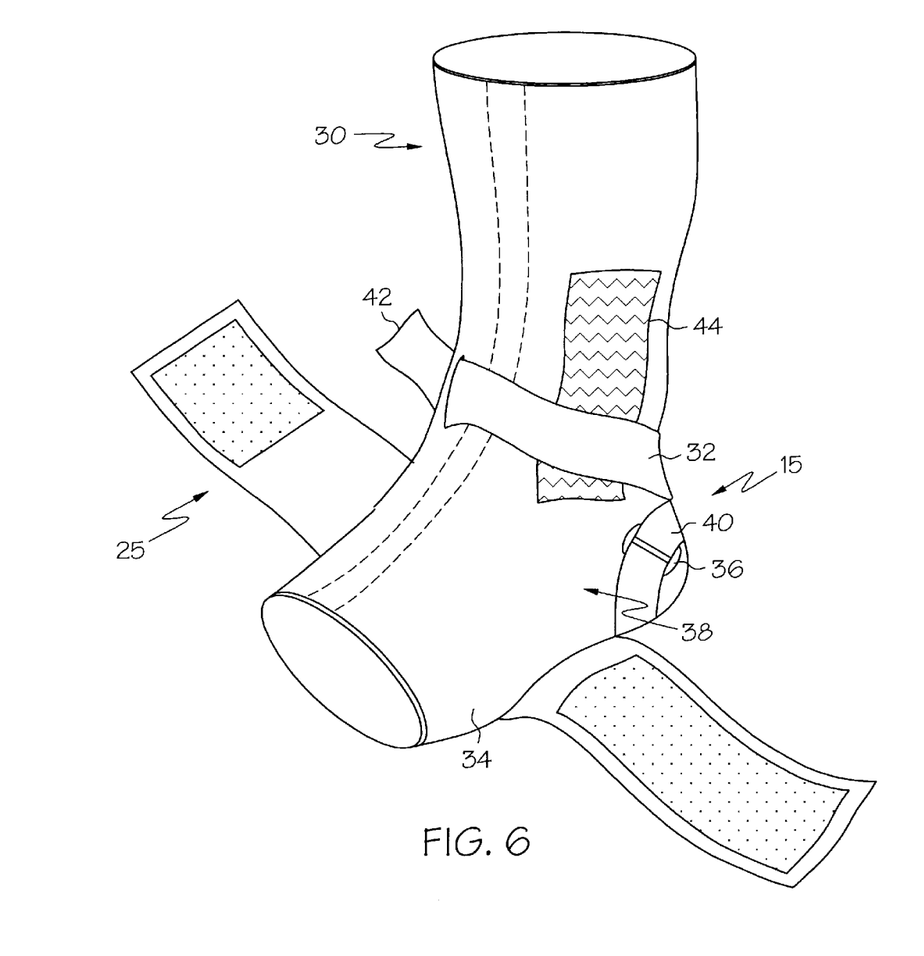
FIG. 6 is a perspective view of the embodiment shown in FIG. 3 wherein the sock is shown with the primary support mechanism in a secured state.

Once the straps 32 have been disposed about the heel region 38 and sufficiently tightened to apply pressure to the foot, the free ends 42 of the straps 32 may be secured to an ankle region 44 such as is shown in FIG. 6. Preferably, ankle region 44 and straps 32 are at least partially comprised of hook-and-loop material such as Velcro™. As a result the free ends 42 of the straps 32 may be removably engaged to the ankle region 44 as shown. In an alternative embodiment the free ends 42 may be merely tied together about the ankle region 44, or otherwise fastened to ensure the sufficiency of the force supplied by loop 40.

Figure 7:
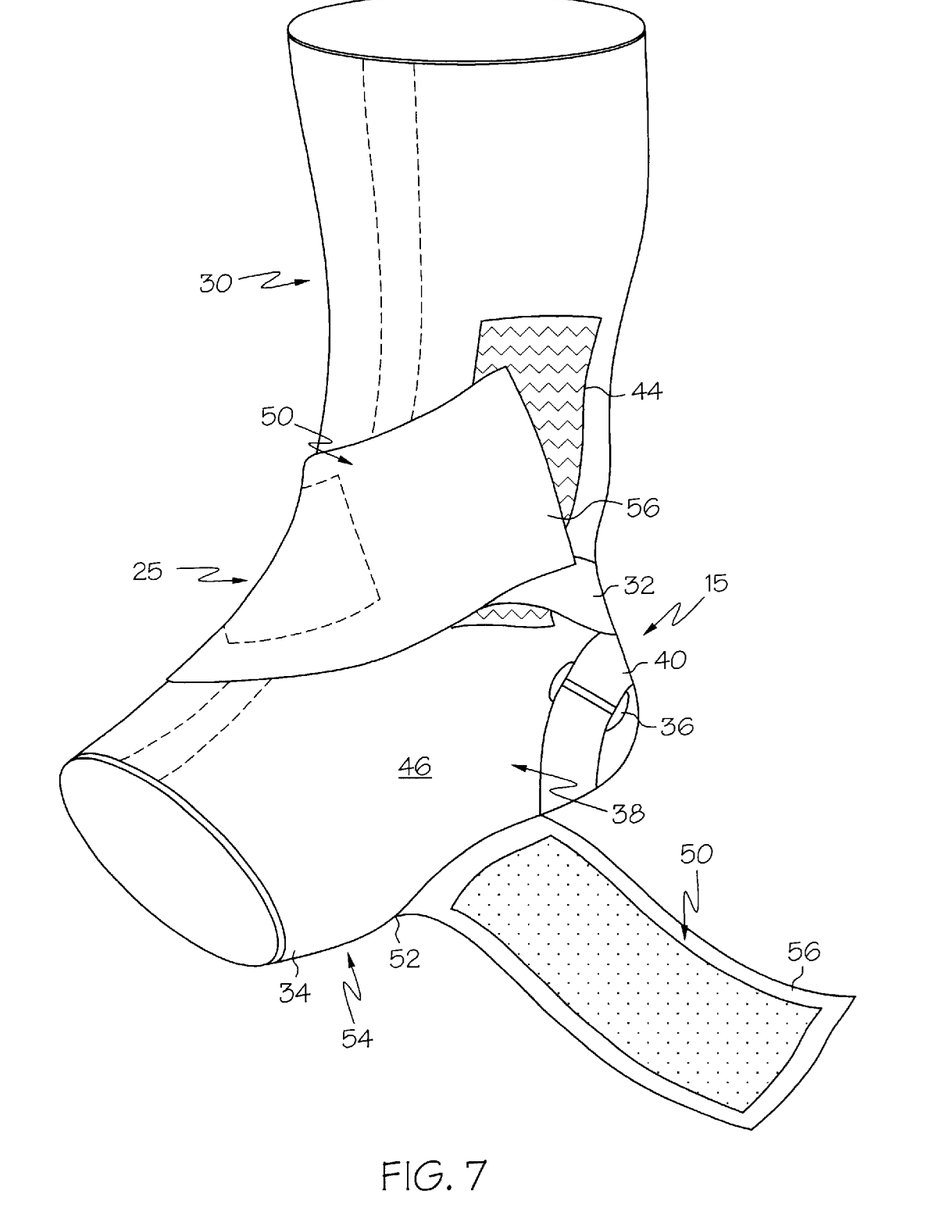
FIG. 7 is a perspective view of the embodiment shown in FIG. 3 wherein the sock is shown with the secondary mechanism being initially secured.

Once the straps 32 form loop 40 and are secured at or about the ankle region 44, the secondary support mechanism 25 may be secured about the arch region 46 of the body 34 such as is shown in FIG. 7. As is shown in FIG. 7, the secondary support mechanism is shown as one or more flaps 50 having a first end 52 secured to the bottom 54 of the sock body 34. The free end 56 of the flap 50 are folded up and about the arch region 46 and are subsequently secured to the ankle region 44 and or each other, such as in the manner shown in FIGS. 7 and 8. This unique fold and engagement configuration ensures that the plantar fascia 20, such as is shown in FIG. 9, is supported in a natural and biomechanical position.

Figure 8:
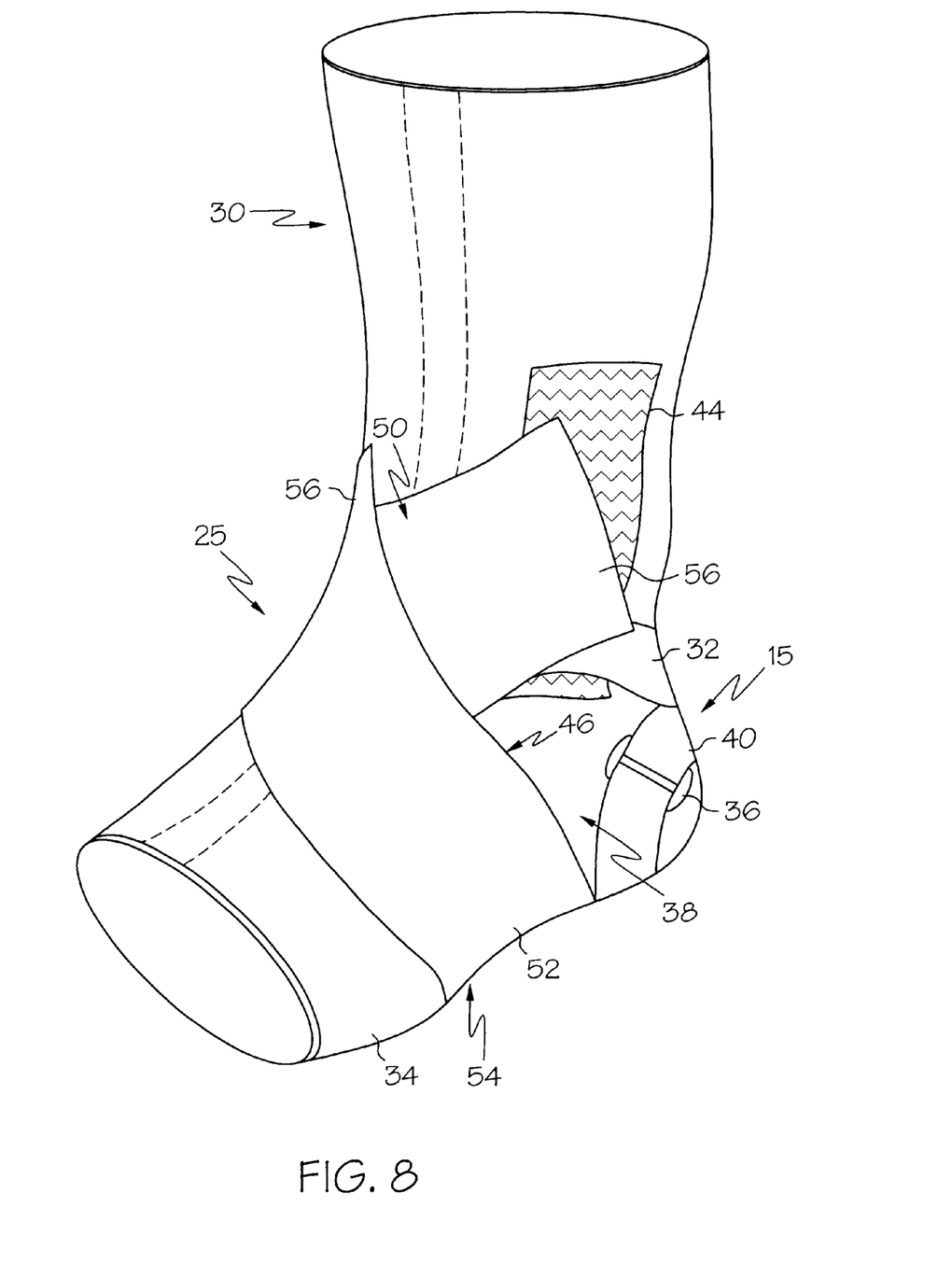
FIG. 8 is a perspective view of the embodiment shown in FIG. 3 wherein the sock is shown with the secondary support mechanism in a secured state.

The effect of the secondary support mechanism 25 is to pull the flap 50 around the medial aspect of the foot 16, whereupon the flap 50 is attached to the top or ankle region 44. This serves to raise the arch 46 and subsequently approximates the forefoot and the heel. This action shortens the plantar fascia 20, thus relieving tension on its insertion into the calcaneus.

As indicated above, the secondary support mechanism 25 is preferably sufficiently flexible to accommodate foot splaying such as a foot experiences during walking. As a result flaps 50 are preferably constructed of a relatively flexible material such as are described above. In order to be removably engaged to the ankle region 44 as well as to themselves, the flaps 50 preferably comprise some type of mechanical engagement material, such as hook-and-loop material previously described.

Figure 9:
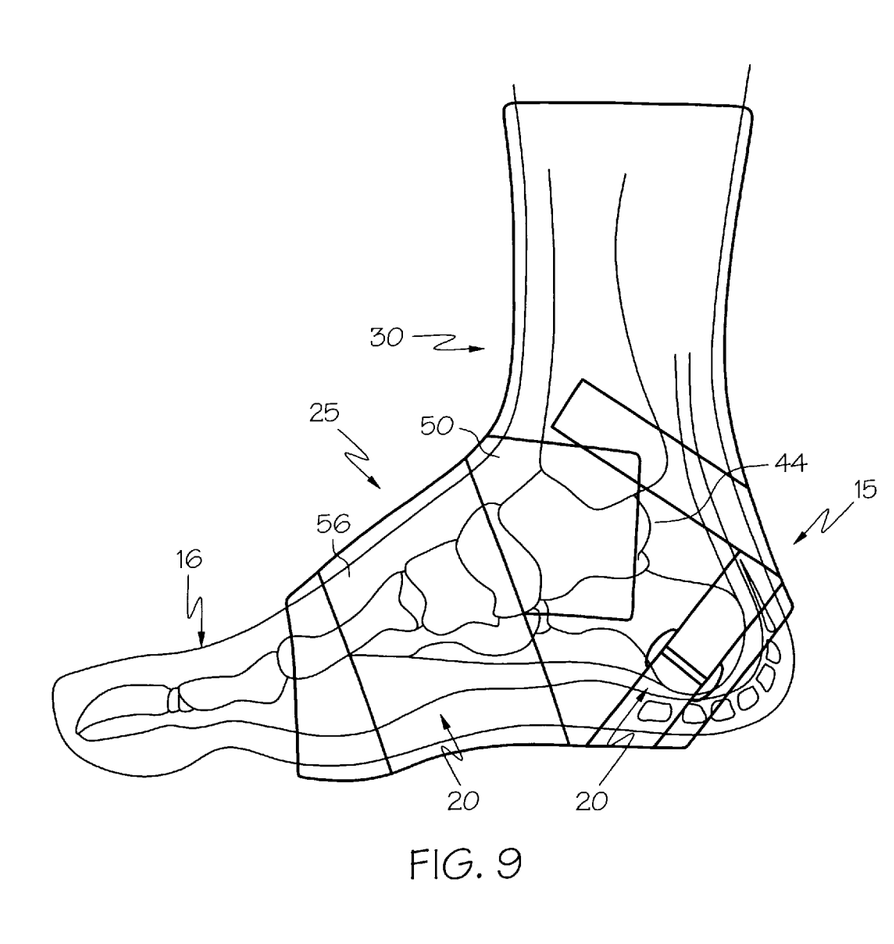
FIG. 9 is a side view of the embodiment shown in FIG. 5 wherein the foot is shown in phantom.

By providing support to the plantar fascia 20, such as is shown in FIG. 9, the sock 30 ensures that the primary and secondary compressive forces of support act to pull the plantar fascia 30 from a first position, common to sufferers of plantar fasciitis, shown in dashed line, to a second position more biomechanically correct position shown in solid line.

While this invention may be embodied in many different forms, there are described in detail herein specific preferred embodiments of the invention. This description is an exemplification of the principles of the invention and is not intended to limit the invention to the particular embodiments illustrated.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. An apparatus designed to be worn on a human foot for the treatment of heel pain, the apparatus comprising:
   a body, the body defining a substantially foot shaped sock having a heel region, an arch region, and an ankle region;
   a first support mechanism, the first support mechanism comprising at least one member having a first end engaged to a portion of the body adjacent to the heel region, the at least one member being adjustably disposable about the heel region;
   at least one adjustment bracket, the at least one member constructed and arranged to be threaded through the at least one adjustment bracket, the at least one adjustment bracket constructed and arranged to allow the at least one member to be adjustably tightened about the heel region; and
   a second support mechanism, the second support mechanism comprising at least one flap having a first end engaged to a portion of the body adjacent to the arch region, the at least one flap being adjustably disposable about the arch region;
   when the at least one member is tightened about the heel region, the apparatus provides the heel region with a compressive force, the compressive force placing a plantar fascia of the human foot in a substantially normal biomechanical position.

2. The apparatus of claim 1 wherein at least a portion of the ankle region defines a mechanical securement area constructed and arranged to removably engage a second end of the at least one member.

3. The apparatus of claim 2 wherein the mechanical securement area is constructed and arranged to removably engage a second end of the at least one flap.

4. The apparatus of claim 3 wherein the mechanical securement area is removably secured to the second end of the at least one member, and the second end of the at least one flap by hook-and-loop material.

5. The apparatus of claim 1 wherein the body is at least partially constructed from an elastic material selected from at least one member of the group consisting of: laminate material, neoprene, elastic cotton, rubber, foam rubber, latex, and any combination thereof.

6. The apparatus of claim 1 wherein the at least one member is at least partially constructed from an elastic material selected from at least one member of the group consisting of: laminate material, neoprene, elastic cotton, rubber, foam rubber, latex, and any combination thereof.

7. The apparatus of claim 1 wherein the at least one flap is at least partially constructed from a substantially non-elastic material selected from the group consisting of: cotton, canvas, vinyl, nylon and any combination thereof.

8. The apparatus of claim 1 wherein at least a portion of the at least one flap is more flexible than the at least one member.

9. The apparatus of claim 1 wherein the at least one member is adjustably disposable about a heel region of the human foot and the at least one flap is adjustably disposable about an arch region of the human foot.

10. The apparatus of claim 9 wherein the human foot comprises a plantar fascia, when the at least one member is disposed about the heel region of the human foot and when the at least one flap is disposed about the arch region of the human foot, the sock supports the plantar fascia in a substantially normal biomechanical position.

* * * * *